United States Patent
Suda et al.

(10) Patent No.: US 8,418,942 B2
(45) Date of Patent: Apr. 16, 2013

(54) OXIDATION AND REDUCTION FINE PARTICLES GENERATOR

(75) Inventors: Hiroshi Suda, Takatsuki (JP); Masaharu Machi, Shijonawate (JP); Yasunori Matsui, Omihachiman (JP); Takayuki Nakada, Hikone (JP)

(73) Assignee: Panasonic Corporation, Osaka (JP)

( * ) Notice: Subject to any disclaimer, the term of this patent is extended or adjusted under 35 U.S.C. 154(b) by 262 days.

(21) Appl. No.: 12/745,795

(22) PCT Filed: Dec. 24, 2008

(86) PCT No.: PCT/JP2008/073461
§ 371 (c)(1),
(2), (4) Date: Jun. 2, 2010

(87) PCT Pub. No.: WO2009/081945
PCT Pub. Date: Jul. 2, 2009

(65) Prior Publication Data
US 2010/0243766 A1    Sep. 30, 2010

(30) Foreign Application Priority Data
Dec. 25, 2007 (JP) ................... 2007-332899
Sep. 25, 2008 (JP) ................... 2008-246917

(51) Int. Cl.
*B05B 5/00* (2006.01)
(52) U.S. Cl.
USPC .......................... 239/692; 239/690
(58) Field of Classification Search .......... 361/227, 361/228; 239/690–708
See application file for complete search history.

(56) References Cited

U.S. PATENT DOCUMENTS

| 2004/0053571 A1* | 3/2004 | Aoki et al. ............... 454/159 |
| 2005/0028254 A1* | 2/2005 | Whiting ..................... 4/213 |
| 2009/0127357 A1 | 5/2009 | Suda et al. |

FOREIGN PATENT DOCUMENTS

| JP | 2003-130537 A |   | 5/2003 |
| JP | 2004-97752 A |   | 4/2004 |
| JP | 2005131549 A | * | 5/2005 |
| JP | 2006-046729 A |   | 2/2006 |
| JP | 2006-314365 A |   | 11/2006 |
| JP | 2007-144425 A |   | 6/2007 |
| JP | 2007-167796 A |   | 7/2007 |

OTHER PUBLICATIONS

International Search Report for the Application No. PCT/JP2008/073461 mailed Mar. 3, 2009.
Japanese Office Action issued in Japanese Patent Application No. 2008-246917 mailed on Jan. 8, 2013.

* cited by examiner

*Primary Examiner* — Len Tran
*Assistant Examiner* — Viet Le
(74) *Attorney, Agent, or Firm* — McDermott Will & Emery LLP

(57) ABSTRACT

An oxidation and reduction fine particles generator includes an atomization electrode, a water feeder for supplying water to the atomization electrode and a high voltage generator, and also includes a switch device and a controller. The switch device changes an operation mode to an oxidation mode or a reduction mode. The controller generates negatively charged fine water particles including radicals through electrostatic atomization by applying a high voltage to water supplied to the atomization electrode in the oxidation mode. The controller also inactivates and activates the water feeder and the high voltage generator, respectively to generate reduction fine particles from the atomization electrode by dry discharge in the reduction mode.

15 Claims, 5 Drawing Sheets

OXIDATION AND REDUCTION FINE PARTICLES GENERATOR

TECHNICAL FIELD

The invention relates to an oxidation and reduction fine particles generator for selectively producing oxidation fine particles and reduction fine particles.

BACKGROUND ART

A conventional electrostatic atomizer has an atomization electrode and a supplying device configured to supply water to the atomization electrode. The atomizer is configured to produce electrostatically charged minute water particles in nanometer size through electrostatic atomization by applying a high voltage to the water supplied to the atomization electrode.

The minute water particles are radical oxide such as hydroxyl radicals, which is known to have deodorant efficacy, or elimination and depression effect of virus and fungus.

If the minute water particles are also attached and penetrated to food, an effect such as sterilization, deodorization, decomposition of hazardous material, or moisture retention is obtained. For example, in the technology described in Japanese Patent Application Publication Number 2007-167796, sterilization, deodorization, decomposition of hazardous material, or moisture retention is performed by electrostatically charged minute water particles, namely oxidation fine particles, and thereby food preservation is performed.

By the way, in object deterioration including food, there is not only deterioration caused by fungus as identified above but also deterioration by oxidation.

Therefore, in the aforementioned conventional example, even if deterioration by fungus can be reduced, there is a problem that deterioration by oxidation cannot be reduced.

DISCLOSURE OF THE INVENTION

It is an object of the present invention to selectively produce oxidation fine particles and reduction fine particles.

An oxidation and reduction fine particles generator of the present invention comprises an atomization electrode, a water feeder configured to supply water to the atomization electrode, a high voltage generator configured to apply a high voltage to the atomization electrode, and a controller configured to control the water feeder and the high voltage generator. In an aspect of the invention, the oxidation and reduction fine particles generator further comprises a switch device configured to change an operation mode to an oxidation mode or a reduction mode. The controller is also configured: to generate negatively charged minute water particles including radicals through electrostatic atomization by activating each of the water feeder and the high voltage generator to apply a high voltage to the water supplied to the atomization electrode, when the operation mode is changed to the oxidation mode, and also to inactivate and activate the water feeder and the high voltage generator, respectively to generate reduction fine particles from the surface of the atomization electrode by dry discharge, when the operation mode is changed to the reduction mode.

In the invention, when the operation mode is changed to the oxidation mode, negatively charged minute water particles including radicals (e.g., [·OH], [·$O_2$]) are generated. Accordingly, it is possible to perform sterilization, deodorization, decomposition of hazardous material and so on. When the operation mode is changed to the reduction mode, reduction fine particles are generated. Accordingly, the oxidation of a physical object is restrained, and degradation caused by oxidation can be prevented.

In an embodiment, the atomization electrode is one electrode commonly used in each of the oxidation and reduction modes. In this instance, the configuration is simple, and oxidation fine particles and reduction fine particles can be generated selectively.

In an embodiment, the atomization electrode comprises a first electrode to which a high voltage is applied in the oxidation mode, and a second electrode to which a high voltage is applied in the reduction mode. The first and second electrodes are mutually separated. In this construction, even if the operation mode is changed from the oxidation mode to the reduction mode, the water feeder supplies no water to the second electrode and accordingly reduction fine particles can be generated reliably from the surface of the second electrode. When the operation mode is changed from the reduction mode to the oxidation mode, if water has been supplied to the first electrode, negatively charged minute water particles including radicals can be generated immediately.

In an embodiment, the water feeder is a heat exchanger having a cooling part. The heat exchanger is configured to supply water to the tip of the atomization electrode by cooling the cooling part to form dew out of moisture in the air when it is activated in the oxidation mode. In this construction, water is automatically supplied in the oxidation mode and thereby minute water particles can be produced stably. The water supply is automatically stopped in the reduction mode and thereby energy can be saved.

In an embodiment, the oxidation and reduction fine particles generator further comprises a photodetector configured to detect ambient brightness to obtain a detection value. The switch device is configured: to change the operation mode to the oxidation mode if the detection value is a value equal to or brighter than a predetermined brightness; and also to change the operation mode to the reduction mode if the detection value is a value darker than the predetermined brightness. In this construction, if the detection value is a value equal to brighter than the predetermined brightness, it can be assumed that a human(s) is in action. In this instance, if the operation mode is changed to the oxidation mode, it is possible to remove the odor generated by the human action in addition to sterilization, decomposition of hazardous material and so on. If the detection value is a value darker than the predetermined brightness, it can be assumed that a human(s) is in non-action (asleep). In this instance, if the operation mode is changed to the reduction mode, it is possible to prevent degradation of skin and hair of a human(s) asleep, namely to preserve the skin's and hair's moisture.

In an embodiment, the oxidation and reduction fine particles generator further comprises an odor sensor configured to detect an ambient odor to obtain a detection value. The switch device is configured: to change the operation mode to the oxidation mode if the detection value is a value equal to or stronger than a predetermined odor; and also to change the operation mode to the reduction mode if the detection value is a value weaker than the predetermined odor. In this construction, if the detection value is a value equal to stronger than the predetermined odor, it can be assumed that a human(s) is in action to generate odor. In this instance, if the operation mode is changed to the oxidation mode, it is possible to remove the odor generated by the human action in addition to sterilization, decomposition of hazardous material and so on. If the detection value is a value weaker than the predetermined odor, it can be assumed that a human(s) is in non-action (asleep). In this instance, if the operation mode is changed to the reduction mode, it is possible to prevent degradation of skin and hair of a human(s) asleep, namely to preserve the skin's and hair's moisture.

In an embodiment, the oxidation and reduction fine particles generator further comprises a human body detection sensor for detecting human movement. The switch device is configured; to change the operation mode to the oxidation mode if the human body detection sensor detects human movement; and also to change the operation mode to the reduction mode if the human body detection sensor does not detect human movement. In this construction, if the human body detection sensor detects human movement, the operation mode is changed to the oxidation mode.

Accordingly, it is possible to remove the odor generated by the human action in addition to sterilization, decomposition of hazardous material and so on. Unless the human body detection sensor detects human movement, the operation mode is changed to the oxidation mode. Accordingly, it is possible to prevent degradation of skin and hair of a human(s) asleep, namely to preserve the skin's and hair's moisture.

BRIEF DESCRIPTION OF THE DRAWINGS

Preferred embodiments of the invention will now be described in further details. Other features and advantages of the present invention will become better understood with regard to the following detailed description and accompanying drawings where.

BEST MODE FOR CARRYING OUT THE INVENTION

An oxidation and reduction fine particles generator in accordance with an embodiment of the present invention is explained. The oxidation and reduction fine particles generator has an atomization electrode 1, a water feeder 2, a high voltage generator 3 and a controller 10. The water feeder 2 is configured to supply water to the atomization electrode 1. The high voltage generator 3 is configured to apply a high voltage to the atomization electrode 1. The controller 10 is configured to control the water feeder 2 and the high voltage generator 3. In an aspect, the oxidation and reduction fine particles generator further includes a switch device. The switch device is configured to change an operation mode to an oxidation mode or a reduction mode. The controller 10 is configured to generate negatively charged minute water particles including radicals through electrostatic atomization by activating each of the water feeder 2 and the high voltage generator 3 to apply a high voltage to water supplied to the atomization electrode 1, when the operation mode is changed to the oxidation mode. The controller 10 also inactivate and activate the water feeder 2 and the high voltage generator 3, respectively to generate reduction fine particles from the surface of the atomization electrode 1 by dry discharge, when the operation mode is changed to the reduction mode.

Figure 1:
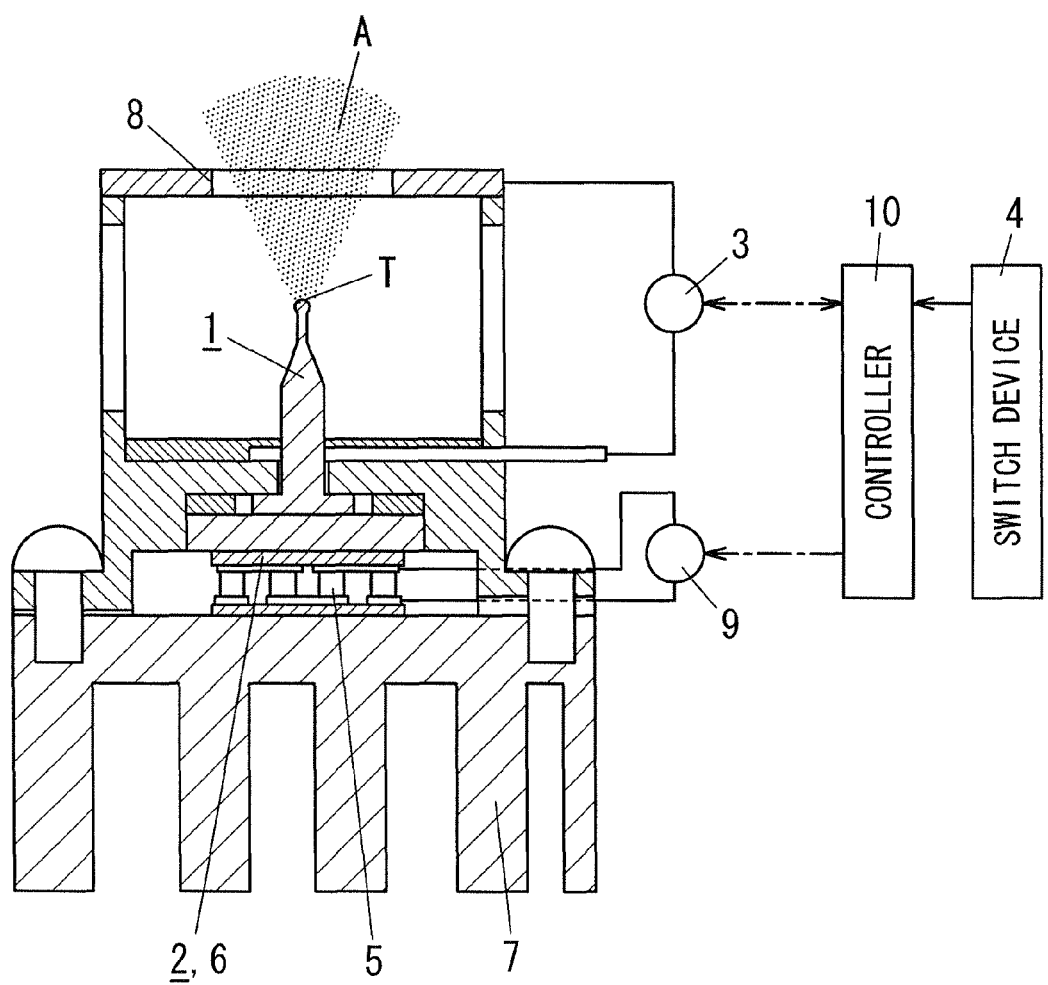
FIG. 1 is an explanatory diagram of an oxidation and reduction fine particles generator in accordance with an embodiment of the present invention.
Figure 2:
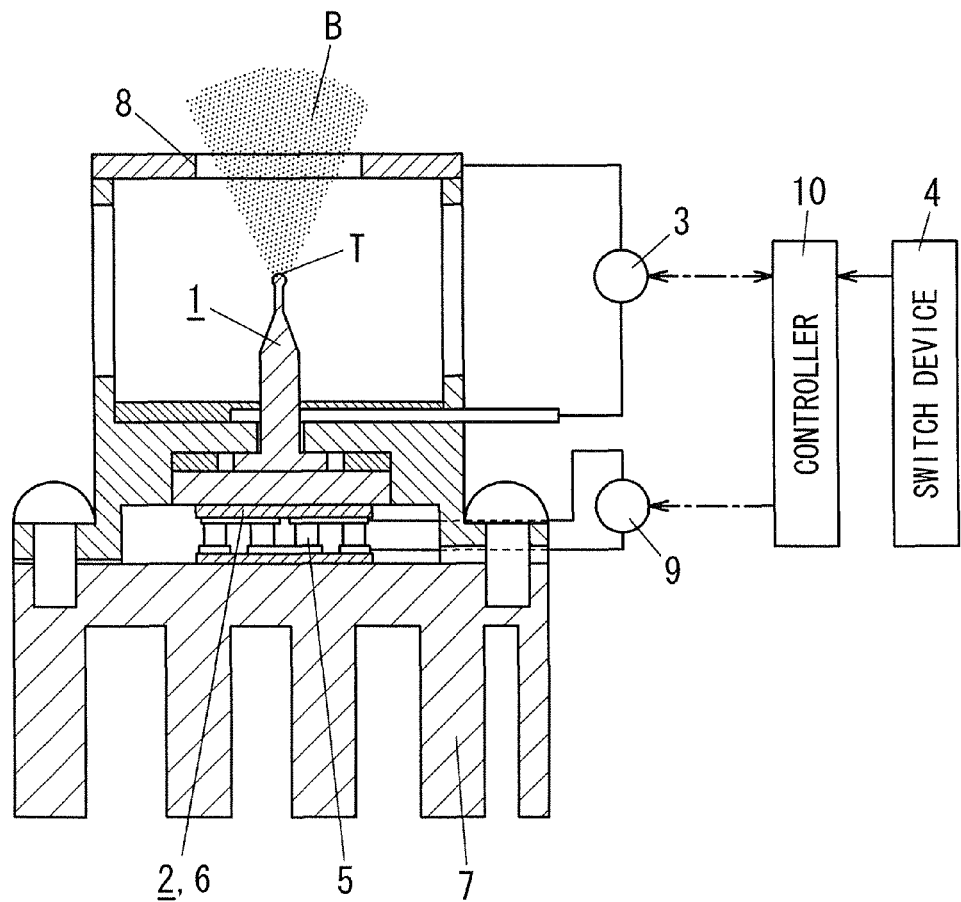
FIG. 2 is an explanatory diagram of a reduction mode of the embodiment.

FIGS. 1 and 2 shows the oxidation and reduction fine particles generator in accordance with an embodiment of the present invention. In this embodiment, the atomization electrode 1 is one electrode commonly used in each of the oxidation and reduction modes, and the surface or the whole part is formed of a reducing substance such as platinum. Therefore, if the operation mode is changed to the reduction mode and then the high voltage generator 3 applies a high voltage to the atomization electrode 1, reduction fine particles are emitted from the surface of the atomization electrode 1 by dry discharge.

The water feeder 2 may be configured: to produce dew condensation water, from moisture in the air, on the tip of the atomization electrode 1; or to supply the tip of the atomization electrode 1 with water stored in a tank through a carrier device.

In the example of FIGS. 1 and 2, the water feeder 2 produces dew condensation water from moisture in the air. A cooling part 6 of a heat exchanger 5 such as a Peltier unit is connected to the atomization electrode 1, and a Peltier unit power supply 9 energizes the Peltier unit. Thereby, the atomization electrode 1 is cooled by the cooling part 6, and dew condensation water is supplied to the atomization electrode 1 by moisture in the air. In FIGS. 1 and 2, 7 is a radiator of the heat exchanger 5 such as a Peltier unit.

In an example, the cooling part 6 of the heat exchanger 5 cools a cold plate (not shown) to produce dew condensation water on the cold plate and a carrier device supplies the dew condensation water to the atomization electrode 1.

In FIGS. 1 and 2, an opposite electrode 8 is provided so as to face the tip of the atomization electrode 1. A first end of the high voltage generator 3 is connected to the atomization electrode 1, and its second end is connected to the opposite electrode 8. However, not limited to this, the opposite electrode 8 may be connected to a frame ground (e.g., a frame of electrical equipment or the like incorporating the oxidation and reduction fine particles generator of the present invention). The frame itself may be provided as an electrode without providing the opposite electrode 8.

The controller 10 is formed to control the high voltage generator 3 and the Peltier unit power supply 9 by a control signal.

The controller 10 may estimate a discharge state by detecting a discharge current when a high voltage is applied to the atomization electrode 1 and, based on the discharge state, control the high voltage generator 3 and the Peltier unit power supply 9 in the oxidation mode and also control the high voltage generator 3 in the reduction mode.

In the invention, the oxidation mode and the reduction mode are utilized. If the operation mode is the oxidation mode, the controller 10 generates electrostatically charged minute water particles including radicals (A) through electrostatic atomization by applying a high voltage to water supplied to the atomization electrode 1. When the operation mode is the reduction mode, controller 10 applies a high voltage to the atomization electrode 1 without supplying water to the atomization electrode 1 and then discharges reduction fine particles B from the surface of the atomization electrode 1 through dry discharge. Operating the switch device 4 such as a selector switch can change the operation mode to the oxidation mode or the reduction mode.

That is, when the operation is set to the oxidation mode through the switch device 4, the controller 10 turns on each of the high voltage generator 3 and the heat exchanger 5 (i.e., Peltier unit power supply 9). The Peltier unit is then activated and the cooling part 6 cools the atomization electrode 1, thereby producing dew condensation water on the atomization electrode 1 by moisture in the air.

Thus, while the water is supplied to the atomization electrode 1, the high voltage generator 3 applies a minus high voltage to the atomization electrode 1. Thereby, coulomb force acts between the water supplied to the tip of the atomization electrode 1 and the opposite electrode 8 by the high voltage between the atomization electrode 1 and the opposite electrode 8. Then, the fluid level of the water locally rises like a cone, and a Taylor cone is formed. Thus, if the Taylor cone (T) is formed, an electric charge concentrates on the tip of the Taylor cone and then the electrical field intensity at the part becomes large. Thereby, the coulomb force at the part becomes larger and the Taylor cone is further developed. Thus, when the Taylor cone grows up and the electric charge concentrated on the tip of the Taylor cone has a high density, the water on the tip of the Taylor cone receives a large energy (repulsion force by the high density electric charge) and exceeds surface tension to repeat split and scatter (Rayleigh splitting), thereby producing a large amount of electrostatically charged minute water particles (A) in nanometer size that have active species (radicals) and negatively charged. FIG. 1 shows the operation of the oxidation mode.

When a high voltage is applied to the water supplied to the tip of the atomization electrode 1, free radicals such as [·H], [·OH], [·$O_2$] are generated by energy of the high voltage. At this time, if a minus high voltage is applied to the atomization electrode, electrons (e⁻) are supplied from the atomization electrode 1 to the part of the Taylor cone. Accordingly, [·H] is coupled with an electron to become $H_2$ and [·OH], [·$O_2$] remain, so that electrostatically charged minute water particles including active oxygen are obtained by electrostatic atomization. Therefore, the negatively charged minute water particles are oxidation fine particles including free radicals such as [·OH], [·$O_2$] and can perform sterilization, deodorization, decomposition of hazardous material and so on by the free radicals such as [·OH], [·$O_2$]. The electrostatically charged minute water particles (A) are nanometer in size and extremely small, and therefore can float widely and deeply penetrate into the inside of objects such as clothes, thereby producing effects such as the aforementioned sterilization, deodorization, decomposition of hazardous material. The electrostatically charged minute water particles (A) in nanometer size can also penetrate into the inside of food such as vegetables, fruit, meat and produce moisturizing action. It is also possible to penetrate into the inside of the human skin and produce moisturizing action.

On the other hand, if the operation mode is changed to the reduction mode by operating the switch device 4, the controller 10 turns the high voltage generator 3 on and turns the heat exchanger 5 off. In this instance, a high voltage is applied to the atomization electrode 1 and reduction fine particles (B) are generated from the surface of the atomization electrode 1 by dry discharge. FIG. 2 shows the operation of the reduction mode.

In the invention, the reduction mode includes not only the reduction of oxidized object(s) but also antioxidation. That is, the oxidation of a substance M is M+O→MO, while the antioxidation is M+O+X→M+XO.

The reduction fine particles (B) generated in this manner can restrain the oxidation of a physical object to prevent degradation caused by oxidation. For example, if the reduction fine particles (B) are attached to food such as vegetables, fruit, meat, fishes, the oxidation of the food and therefore food oxidative degradation can be restrained. It is also possible to restrain aging of human tissue caused by oxidation.

In an example, when food is preserved, the sterilization, deodorization, decomposition of hazardous material as well as moisture retention may be performed by setting the operation mode to the oxidation mode to attach the electrostatically charged minute water particles including radicals (A) to the food. Subsequently, food oxidative degradation may be restrained by changing the operation mode to the reduction mode to attach the reduction fine particles (B) to the food after the sterilization, deodorization, decomposition of hazardous material as well as moisture retention.

This can provide prolonged preservation while maintaining freshness in comparison with only attachment of the electrostatically charged minute water particles including radicals (A) to the food, or only attachment of the reduction fine particles (B) to the food.

As stated above, if one atomization electrode 1 is used in each of the oxidation mode and the reduction mode, it is possible to reduce the number of parts and compact the generator. In this instance, considering acid resistance, platinum is preferable to a substance having reducing capacity for forming all or a surface of the atomization electrode 1. The other metal is not preferable because metallic particles having reducing capacity may be mixed in the electrostatically charged minute water particles A having oxidative power in the oxidation mode. However, not limited to one atomization electrode 1, the atomization electrode of the invention may include a first electrode to which a high voltage is applied in the oxidation mode and a second electrode to which a high voltage is applied in the reduction mode. The first and second electrodes may be mutually separated.

Figure 3:
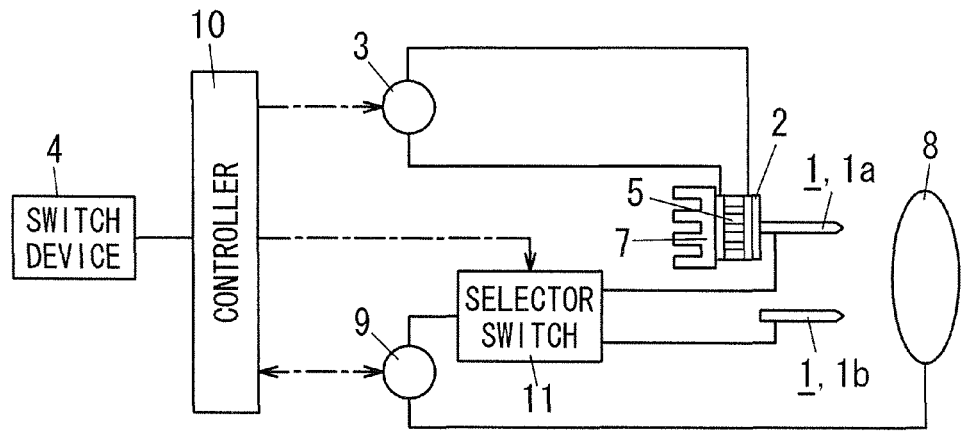
FIG. 3 is a schematic diagram of an explanatory diagram of an oxidation and reduction fine particles generator in accordance with an embodiment of the present invention.

FIG. 3 shows an embodiment including first and second electrodes 1a and 1b. In FIG. 3, 11 is a selector switch. In the oxidation mode, the controller 10 turns on the heat exchanger 5 (i.e., Peltier unit power supply 9), and also turns on the high voltage generator 3 while controlling the selector switch 11 to apply a high voltage to the first electrode 1a, thereby generating the electrostatically charged minute water particles (A) which are nanometer in size and include radicals.

In the reduction mode, the controller 10 turns on the heat exchanger 5 (i.e., Peltier unit power supply 9), and also turns on the high voltage generator 3 while controlling the selector switch 11 to apply a high voltage to the second electrode 1b, thereby generating the reduction fine particles (B) through dry discharge.

In this embodiment, when the operation mode is changed from the oxidation mode to the reduction mode through the switch device 4, the water feeder 2 does not supply water to the second electrode 1b and accordingly can reliably generate the reduction fine particles (B) from the surface of the second electrode 1b.

When the operation mode is changed from the reduction mode to the oxidation mode, if water has been supplied to the first electrode 1a, electrostatically charged minute water particles including radicals (A) can be generated immediately.

Figure 4A:
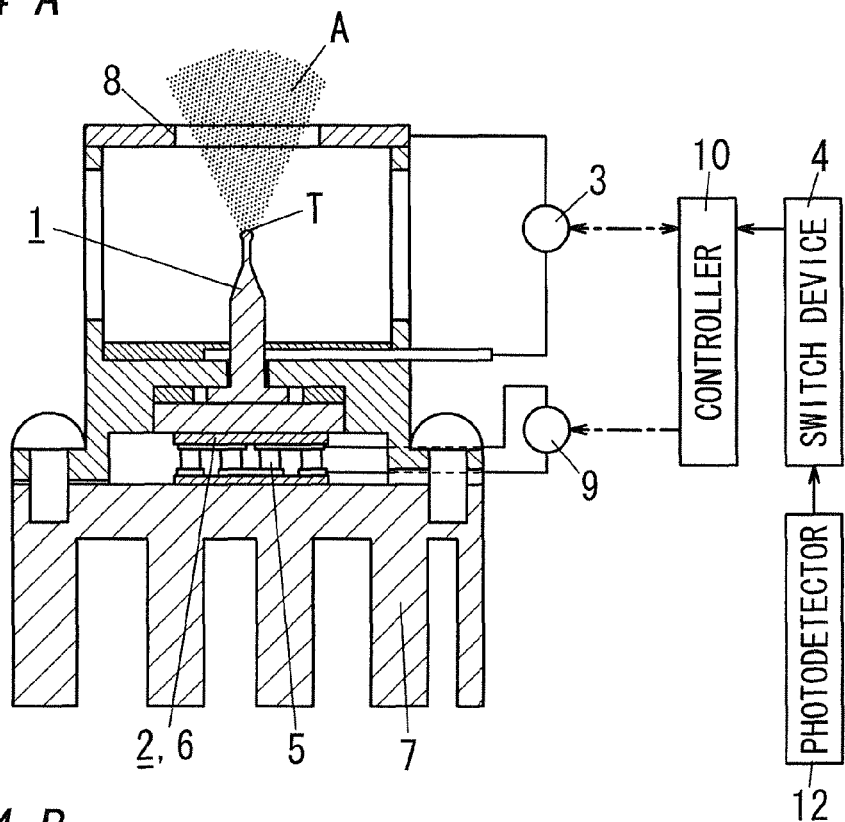
FIG. 4A is an explanatory diagram of an oxidation mode of an oxidation and reduction fine particles generator in accordance with an embodiment of the present invention.
Figure 4B:
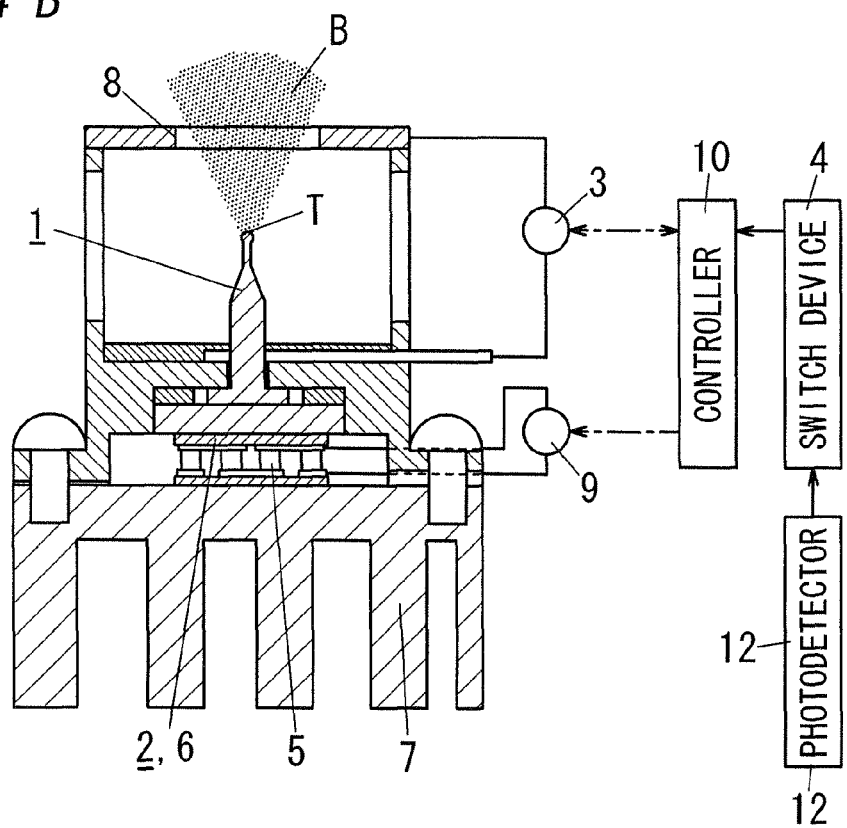
FIG. 4B is an explanatory diagram of a reduction mode of the embodiment.

FIGS. 4A and 4B show an oxidation and reduction fine particles generator in accordance with an embodiment of the present invention. For example, like FIGS. 1 and 2, the embodiment has an atomization electrode 1, a water feeder 2, a high voltage generator 3, a switch device 4, a heat exchanger 5 (a cooling part 6 and a radiator 7), an opposite electrode 8, a Peltier unit power supply 9 and a controller 10, and is installed indoors. In an aspect of the embodiment, the oxidation and reduction fine particles generator further includes a photodetector 12 configured to detect ambient brightness to obtain a detection value. The switch device 4 is configured: to change the operation mode to the oxidation mode if the detection value is a value equal to brighter than a predetermined brightness; and also to change the operation mode to the reduction mode if the detection value is a value darker than the predetermined brightness. The aspect can be applied to the embodiment of FIG. 3.

If the detection value is a value equal to brighter than the predetermined brightness (predetermined value), it can be assumed that a human(s) is in action. In this instance, as shown in FIG. 4A, the switch device 4 changes the operation mode to the oxidation mode. Thereby, it is possible to remove the odor generated by the human action in addition to sterilization, decomposition of hazardous material and so on.

If the detection value is a value darker than the predetermined brightness, it can be assumed that a human(s) is in non-action (asleep). In this instance, as shown in FIG. 4B, the switch device 4 changes the operation mode to the reduction mode. Thereby, it is possible to prevent degradation of skin and hair of a human(s) asleep, namely to preserve the skin's and hair's moisture.

Figure 5A:
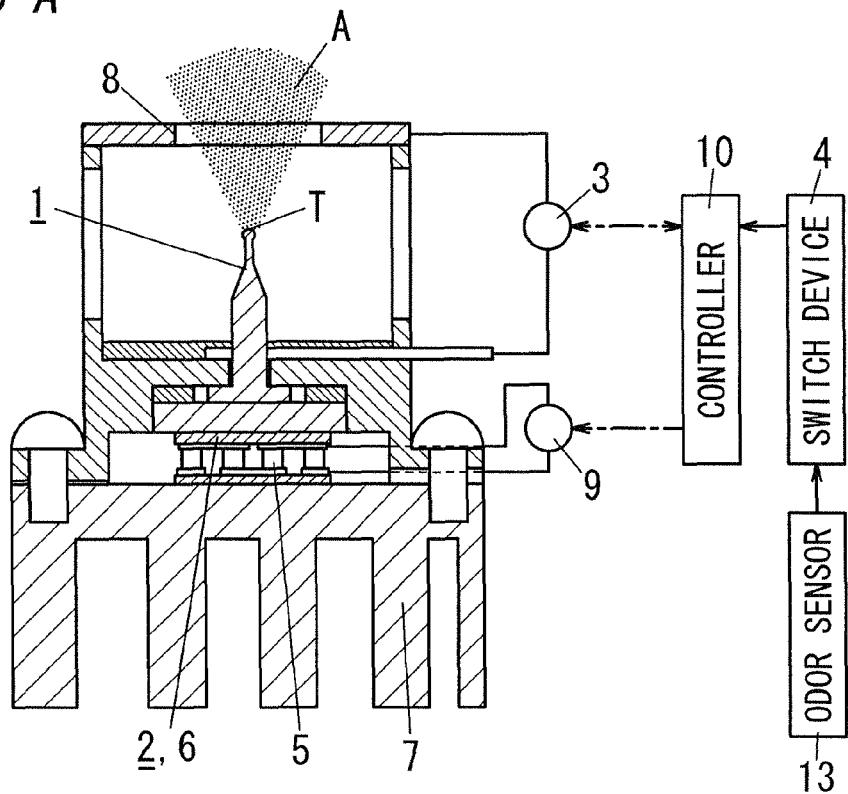
FIG. 5A is an explanatory diagram of an oxidation mode of an oxidation and reduction fine particles generator in accordance with an embodiment of the present invention.
Figure 5B:
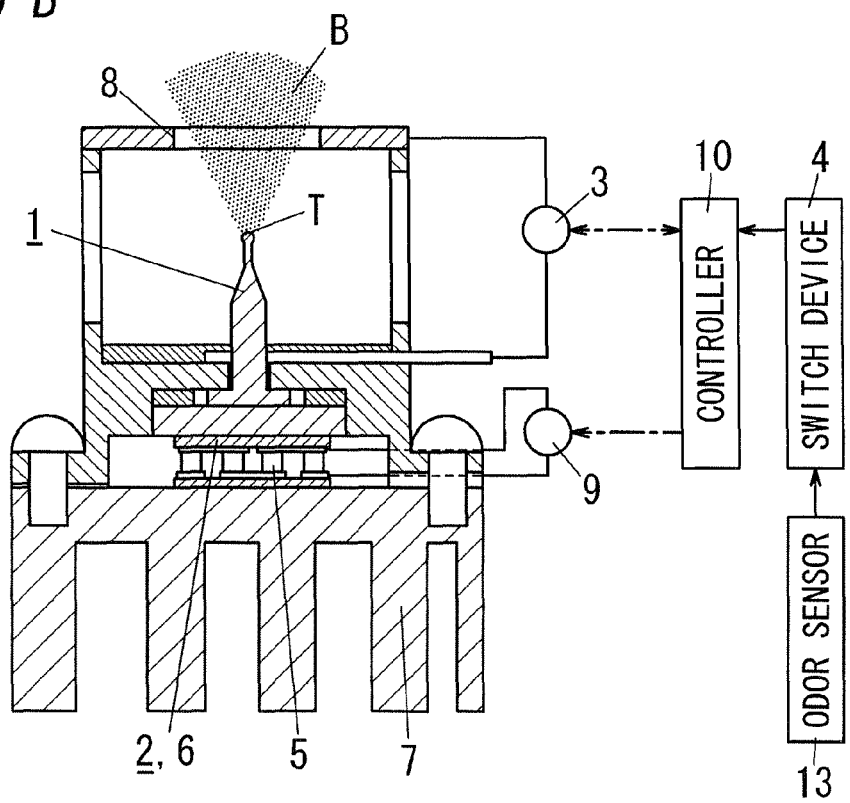
FIG. 5B is an explanatory diagram of a reduction mode of the embodiment.

FIGS. 5A and 5B show an oxidation and reduction fine particles generator in accordance with an embodiment of the present invention. For example, like FIGS. 1 and 2, the embodiment has an atomization electrode 1, a water feeder 2, a high voltage generator 3, a switch device 4, a heat exchanger 5 (a cooling part 6 and a radiator 7), an opposite electrode 8, a Peltier unit power supply 9 and a controller 10, and is installed indoors. In an aspect of the embodiment, the oxidation and reduction fine particles generator further includes an odor sensor 13 configured to detect an ambient odor to obtain a detection value. The switch device 4 is configured: to change the operation mode to the oxidation mode if the detection value is a value equal to stronger than a predetermined odor; and also to change the operation mode to the reduction mode if the detection value is a value weaker than the predetermined odor. The aspect can be applied to the embodiment of FIG. 3.

If the detection value is a value equal to stronger than the predetermined odor (predetermined value), it can be assumed that a human(s) is in action indoors to generate odor. In this instance, as shown in FIG. 5A, the switch device 4 changes the operation mode to the oxidation mode. Thereby, it is possible to remove the odor generated by the human action in addition to sterilization, decomposition of hazardous material and so on.

If the detection value is a value weaker than the predetermined odor, it can be assumed that a human(s) is in non-action (asleep). In this instance, as shown in FIG. 5B, the switch device 4 changes the operation mode to the reduction mode. Thereby, it is possible to prevent degradation of skin and hair of a human(s) asleep, namely to preserve the skin's and hair's moisture.

Figure 6A:
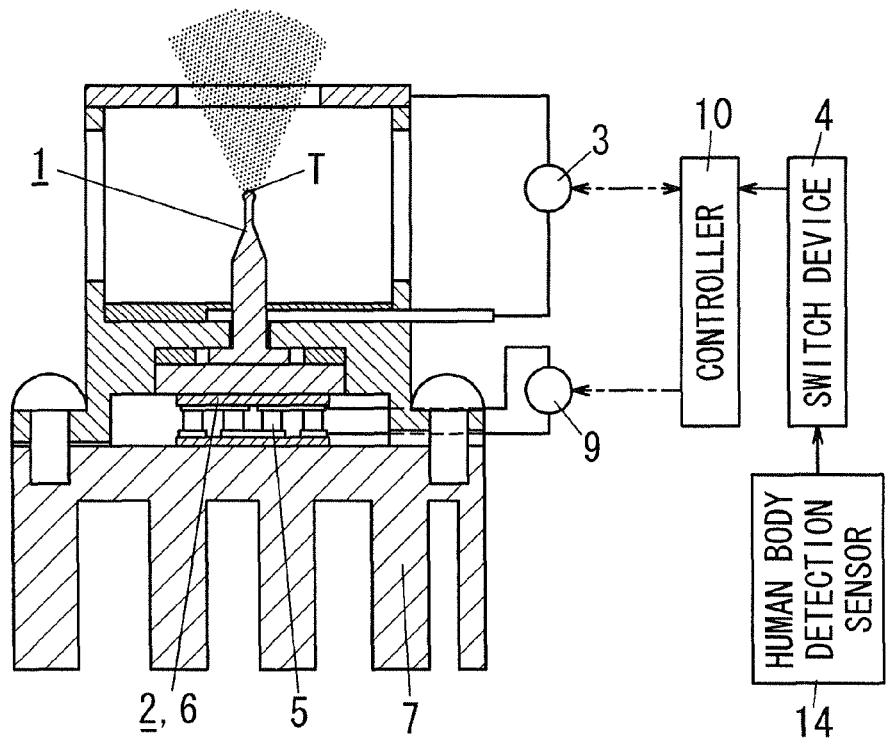
FIG. 6A is an explanatory diagram of an oxidation mode of an oxidation and reduction fine particles generator in accordance with an embodiment of the present invention.
Figure 6B:
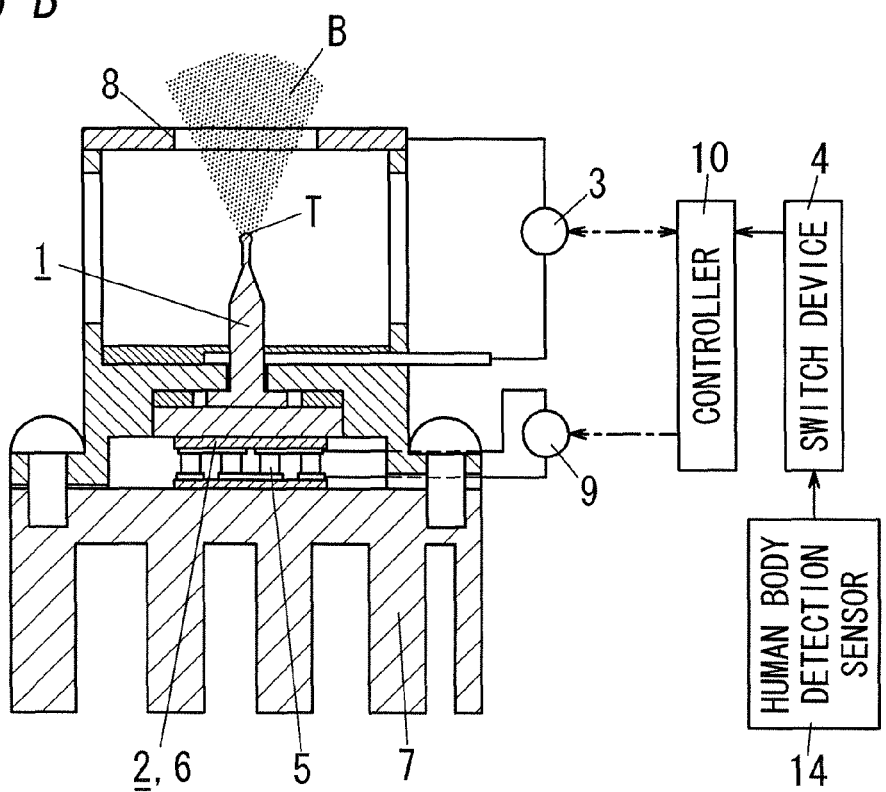
FIG. 6B is an explanatory diagram of a reduction mode of the embodiment.

FIGS. 6A and 6B show an oxidation and reduction fine particles generator in accordance with an embodiment of the present invention. For example, like FIGS. 1 and 2, the embodiment has an atomization electrode 1, a water feeder 2, a high voltage generator 3, a switch device 4, a heat exchanger 5 (a cooling part 6 and a radiator 7), an opposite electrode 8, a Peltier unit power supply 9 and a controller 10, and is installed indoors. In an aspect of the embodiment, the oxidation and reduction fine particles generator further includes a human body detection sensor 14 for detecting human movement. The switch device 4 is configured: to change the operation mode to the oxidation mode if the human body detection sensor 14 detects human movement; and also to change the operation mode to the reduction mode if the human body detection sensor 14 detects few or no human movement. The aspect can be applied to the embodiment of FIG. 3.

If the human body detection sensor 14 detects human movement, the switch device 4 changes the operation mode to the oxidation mode as shown in FIG. 6A. Thereby, it is possible to remove the odor generated by the human action in addition to sterilization, decomposition of hazardous material and so on.

Unless the human body detection sensor 14 substantially detects human movement, the switch device 4 changes the operation mode to the oxidation mode as shown in FIG. 6B. Thereby, it is possible to prevent degradation of skin and hair of a human(s) asleep, namely to preserve the skin's and hair's moisture.

Although the present invention has been described with reference to certain preferred embodiments, numerous modifications and variations can be made by those skilled in the art without departing from the true spirit and scope of this invention.

The invention claimed is:

1. An oxidation and reduction fine particles generator, comprising: an atomization electrode;
    a water feeder configured to supply water to the atomization electrode;
    a high voltage generator configured to apply a high voltage to the atomization electrode; and
    a controller configured to control the water feeder and the high voltage generator,
    wherein the oxidation and reduction fine particles generator further comprises a switch device configured to change an operation mode to an oxidation mode or a reduction mode,
    wherein the controller is configured:
    to generate negatively charged minute water particles including radicals through electrostatic atomization by activating each of the water feeder and the high voltage generator to apply a high voltage to the water supplied to the atomization electrode, when the operation mode is changed to the oxidation mode, and also
    to inactivate and activate the water feeder and the high voltage generator, respectively, to generate reduction fine particles from the surface of the atomization electrode by dry discharge, when the operation mode is changed to the reduction mode.

2. The oxidation and reduction and fine particles generator of claim 1, wherein the atomization electrode is one electrode commonly used in each of the oxidation and reduction modes.

3. The oxidation and reduction fine particles generator of claim 1,
    wherein the atomization electrode comprises a first electrode to which a high voltage is applied in the oxidation mode, and a second electrode to which a high voltage is applied in the reduction mode,
    the first and second electrodes being mutually separated.

4. The oxidation and reduction fine particles generator of claim 1, wherein the water feeder is a heat exchanger that has a cooling part and is configured to supply water to the tip of the atomization electrode by cooling the cooling part to form dew out of moisture in the air when it is activated in the oxidation mode.

5. The oxidation and reduction fine particles generator of claim 1, further comprising a photodetector configured to detect ambient brightness to obtain a detection value,
wherein the switch device is configured:
to change the operation mode to the oxidation mode if the detection value is a value equal to or brighter than a predetermined brightness; and also
to change the operation mode to the reduction mode if the detection value is a value darker than the predetermined brightness.

6. The oxidation and reduction fine particles generator of claim 1, further comprising an odor sensor configured to detect an ambient odor to obtain a detection value,
wherein the switch device is configured:
to change the operation mode to the oxidation mode if the detection value is a value equal to or stronger than a predetermined odor; and also
to change the operation mode to the reduction mode if the detection value is a value weaker than the predetermined odor.

7. The oxidation and reduction fine particles generator of claim 1, further comprising a human body detection sensor for detecting human movement,
wherein the switch device is configured:
to change the operation mode to the oxidation mode if the human body detection sensor detects human movement; and also
to change the operation mode to the reduction mode if the human body detection sensor does not detect human movement.

8. The oxidation and reduction fine particles generator of claim 2, wherein the water feeder is a heat exchanger that has a cooling part and is configured to supply water to the tip of the atomization electrode by cooling the cooling part to form dew out of moisture in the air when it is activated in the oxidation mode.

9. The oxidation and reduction fine particles generator of claim 3, wherein the water feeder is a heat exchanger that has a cooling part and is configured to supply water to the tip of the atomization electrode by cooling the cooling part to form dew out of moisture in the air when it is activated in the oxidation mode.

10. The oxidation and reduction fine particles generator of claim 2, further comprising a photodetector configured to detect ambient brightness to obtain a detection value,
wherein the switch device is configured:
to change the operation mode to the oxidation mode if the detection value is a value equal to or brighter than a predetermined brightness; and also
to change the operation mode to the reduction mode if the detection value is a value darker than the predetermined brightness.

11. The oxidation and reduction fine particles generator of claim 3, further comprising a photodetector configured to detect ambient brightness to obtain a detection value,
wherein the switch device is configured:
to change the operation mode to the oxidation mode if the detection value is a value equal to or brighter than a predetermined brightness; and also
to change the operation mode to the reduction mode if the detection value is a value darker than the predetermined brightness.

12. The oxidation and reduction fine particles generator of claim 2, further comprising an odor sensor configured to detect an ambient odor to obtain a detection value,
wherein the switch device is configured:
to change the operation mode to the oxidation mode if the detection value is a value equal to or stronger than a predetermined odor, and also
to change the operation mode to the reduction mode if the detection value is a value weaker than the predetermined odor.

13. The oxidation and reduction fine particles generator of claim 3, further comprising an odor sensor configured to detect an ambient odor to obtain a detection value,
wherein the switch device is configured:
to change the operation mode to the oxidation mode if the detection value is a value equal to or stronger than a predetermined odor; and also
to change the operation mode to the reduction mode if the detection value is a value weaker than the predetermined odor.

14. The oxidation and reduction fine particles generator of claim 2, further comprising a human body detection sensor for detecting human movement,
wherein the switch device is configured:
to change the operation mode to the oxidation mode if the human body detection sensor detects human movement; and also
to change the operation mode to the reduction mode if the human body detection sensor does not detect human movement.

15. The oxidation and reduction fine particles generator of claim 3, further comprising a human body detection sensor for detecting human movement,
wherein the switch device is configured:
to change the operation mode to the oxidation mode if the human body detection sensor detects human movement; and also
to change the operation mode to the reduction mode if the human body detection sensor does not detect human movement.

* * * * *